(12) United States Patent
Majewski et al.

(10) Patent No.: US 6,643,538 B1
(45) Date of Patent: Nov. 4, 2003

(54) DIRECTIONAL INTRAOPERATIVE PROBE

(75) Inventors: Stanislaw Majewski, Grafton, VA (US); Vladimir Popov, Newport News, VA (US); Georgii Loutts, Chesapeake, VA (US)

(73) Assignee: Southeastern Universities Research Assn., Newport News, VA (US)

( * ) Notice: Subject to any disclaimer, the term of this patent is extended or adjusted under 35 U.S.C. 154(b) by 0 days.

(21) Appl. No.: 09/693,190

(22) Filed: Oct. 20, 2000

(51) Int. Cl.[7] .................................................. A61B 6/00
(52) U.S. Cl. ..................... 600/436; 600/476; 600/113; 600/182; 348/162; 348/165
(58) Field of Search .................................. 600/436, 431, 600/113, 129, 181, 182, 160, 109, 178, 117, 118, 473, 476; 348/162, 65

(56) References Cited

U.S. PATENT DOCUMENTS

| | | | | |
|---|---|---|---|---|
| 4,995,396 A | * | 2/1991 | Inaba et al. | 348/65 |
| 5,014,708 A | * | 5/1991 | Hayashi et al. | 600/105 |
| 5,088,492 A | * | 2/1992 | Takayama et al. | 348/162 |
| 5,749,830 A | * | 5/1998 | Kaneko et al. | 600/109 |

* cited by examiner

Primary Examiner—Marvin M. Lateef
Assistant Examiner—Jeoyuh Lin

(57) ABSTRACT

An introperative surgical probe incorporating both a fiber optic imaging system and multi-element beta/gamma radiation directional indicating system is described.

8 Claims, 2 Drawing Sheets

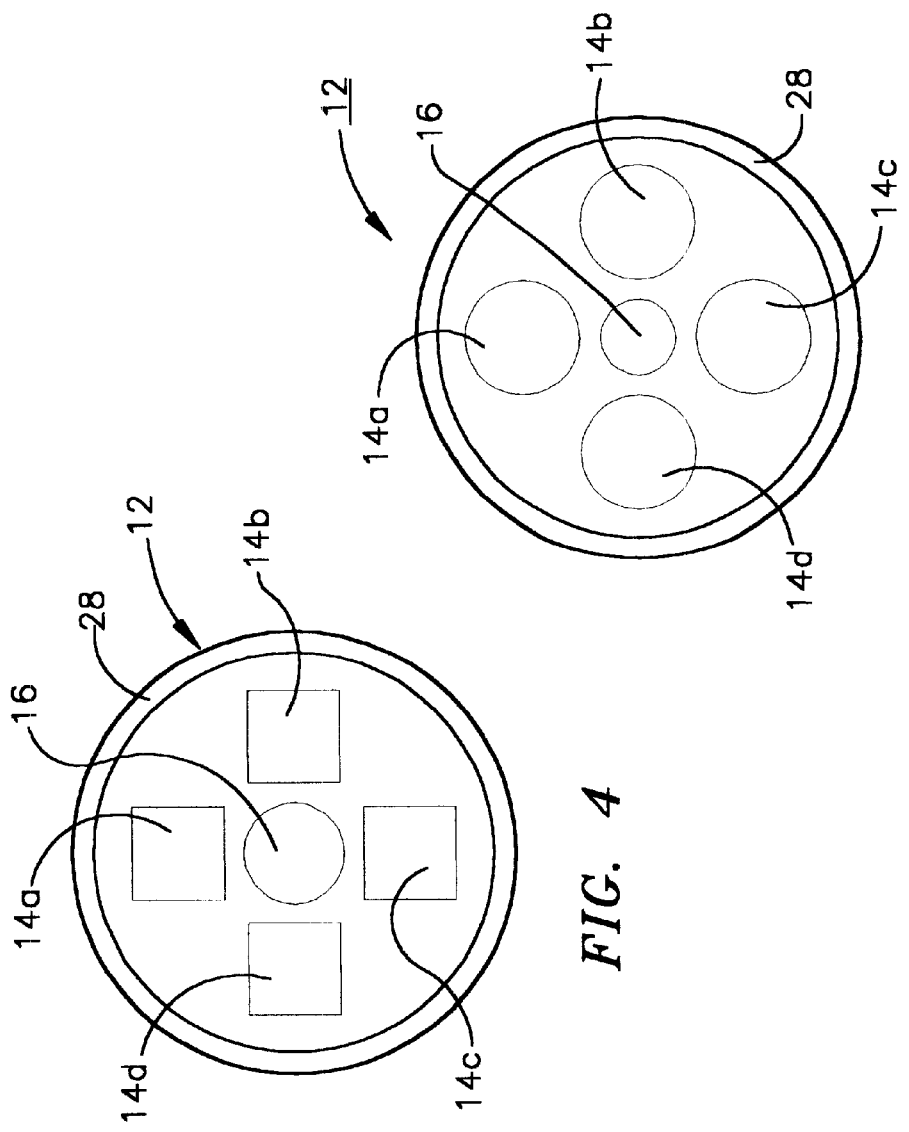
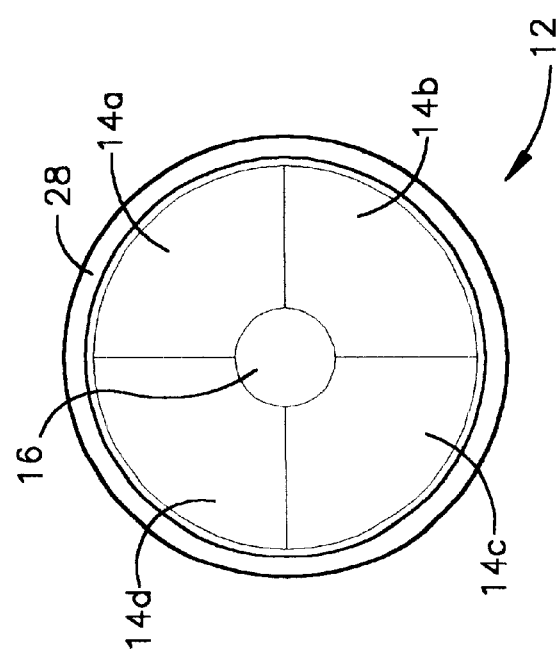
FIG. 5
FIG. 4
FIG. 3

US 6,643,538 B1

DIRECTIONAL INTRAOPERATIVE PROBE

The United States of America may have certain rights in this invention under Management and Operating Contract No. DE-AC05-84ER 40150 from the Department of Energy.

FIELD OF THE INVENTION

The present invention relates to intraoperative surgical probes useful in cancer surgery because of their ability to detect beta and/or gamma radiation and to provide, in the immediate area of the surgery, a signal indicative of proximity to, and therefore the location of, cancerous tissue. A preferred embodiment of the surgical probe of the present invention also provides a simultaneous visual image of the incision.

BACKGROUND OF THE INVENTION

The use of intraoperative probes to assist surgeons in defining the boundaries of cancerous lesions during surgical procedures performed following the injection of the patient with a radiopharmaceutical such as positron labeled fluorodeoxyglucose (FDG), the glucose analog commonly used for Positron Emission Tomography (PET).

One of the most reliable techniques for the detection of cancerous tissue is Positron Emission Tomography (PET) which involves the injection of a surgical patient with fluorodioxyglucose (FDG), a glucose analog that is preferentially taken up by quickly metabolizing cells such as those in the heart, brain and, for current purposes, cancer sites. FDG emits positrons that have a short (~1–2 mm) free path in human tissue before decaying into 511 keV gamma radiation. PET imagers detect these photons and construct a 3-D image of the patient. While these devices are extremely useful, they are, unfortunately, very expensive and very large. Thus, while used in the early detection and localization of cancerous areas, they are of less use in the surgical excision of diseased tissue, because their size makes them far to cumbersome for use in a surgical setting.

A highly desirable surgical probe would therefore be one of sufficiently small size as to truly be an intraoperative probe, which is capable of detecting beta, i.e. positron, emissions from a preferentially metabolized radiopharmaceutical such as FDG. Such a probe that could also selectively detect the 511 keV decay products of positrons would have even further enhanced capabilities for guiding a surgeon to the area of a cancerous lesion using the gamma emissions, and then zeroing in on its exact location, i.e. within about 1–2 mm, using the positron emissions as his/her guide.

U.S. patent application Ser. No. 09/240,239 filed Jan. 30, 1999 describes an intraoperative surgical probe capable of detecting both positrons and gamma-rays that preferably also incorporates visual and/or audible display mechanisms therein such that in the course of a surgical procedure the surgeon does not have to remove his/her eyes from the area of the incision to obtain information regarding proximity to the area identified for excision.

The just-described probe does not, however, provide any visual information regarding the physical structure or condition of the actual area of the incision, information that is equally useful and necessary to the surgeon and which, until now has only been available to the surgeon by observation of the incision directly with his or her eyes during the procedure. This condition often requires a larger incision than would be necessary to provide the required area of direct observation.

A device that incorporated the ability to acquire both directional information and provide a visual view of the internal area of the incision would therefore be highly desirable.

OBJECTS OF THE INVENTION

It is therefore an object of the present invention to provide an intraoperative surgical probe that provides directional information regarding the location of a lesion or other tissue to be removed to the surgeon in the handle or some portion thereof in the immediate vicinity of the incision while also incorporating the ability to provide visual information regarding the physical condition of the area of the incision simultaneously without the need for the surgeon to move or relocate the directional probe.

SUMMARY OF THE INVENTION

According to the present invention, there is provided an intraoperative surgical probe that combines an optical camera and a directional beta/gamma directional probe into a single unit. The leading end of the probe is optically coupled to a CCD camera in the trailing end of the probe by optical fibers located in the center of the probe. Scintillators located in the leading end and surrounding the centrally located imaging optical fibers are connected via light guides or separate optical fibers or rods to photodetectors located in the trailing end of the probe that also incorporates electronics to determine the directional location of the principal sources of radiation relative to the leading end of the probe and a display mechanism for communicating this information to the surgeon. Optical or visual information regarding the incision is communicated via the CCD camera and appropriate cabling to a video monitor in the immediate vicinity of the surgeon to simultaneously communicate the visual information.

DESCRIPTION OF THE DRAWINGS

FIG. 3 is an end view of a preferred scintillator/optical fiber configuration within the leading end of the probe of the present invention.

FIG. 4 is an and view of an alternative scintillator/optical fiber configuration within the leading end of the probe of the present invention.

FIG. 5 is an end view of yet another alternative scintillator/optical fiber configuration within the leading end of the probe of the present invention.

DETAILED DESCRIPTION

According to the present invention, an introperative surgical probe incorporating both a fiber optic imaging system and multi-element beta/gamma radiation directional indicating system is described.

Figure 1:
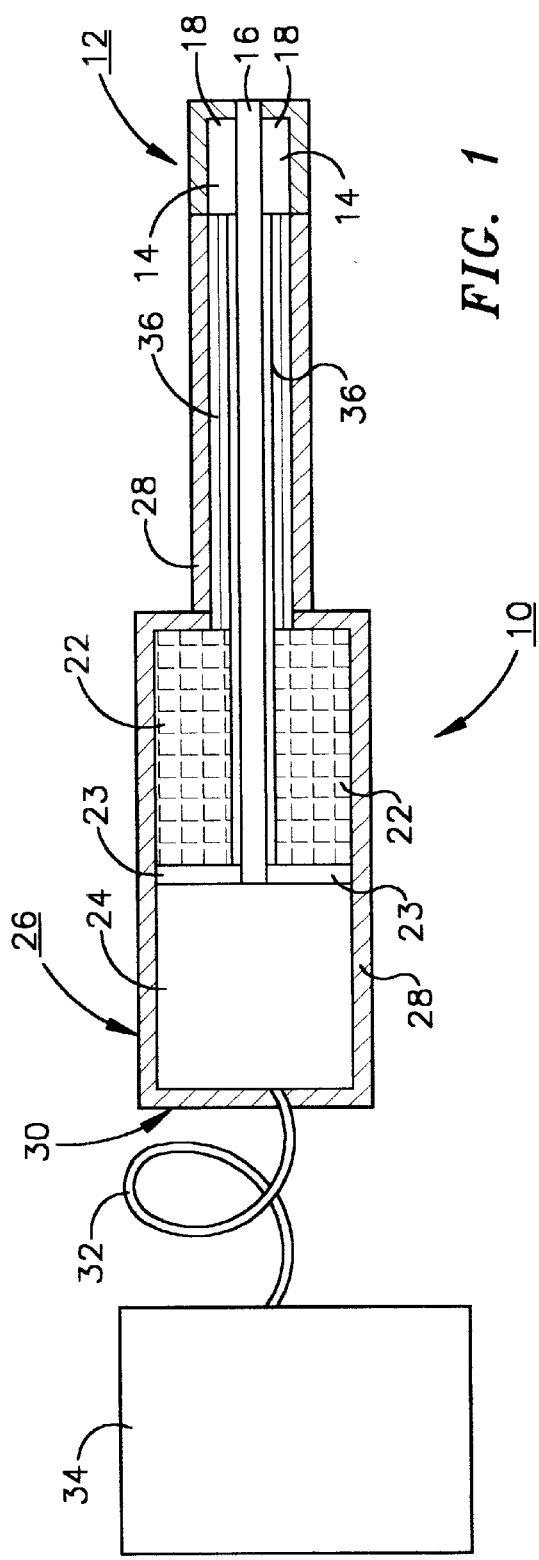
FIG. 1 is a schematic cross-sectional view of a first preferred embodiment of the intraoperative surgical probe of the present invention.

Referring no to FIG. 1 that depicts a first preferred embodiment of the surgical probe of the present invention, surgical probe 10 comprises a leading end 12 that encompasses radiation sensor 14 located as described hereinafter about a centrally located fiber optic imaging guide 16. Radiation sensor 14 is protected behind radiation entrance window 18. Light guides 36 also about centrally located fiber optic imaging guide 16 extend from optical contact with radiation sensor 14 to optical contact with photodetectors 22 while centrally located optical imaging guide 16 extends to and transmits visual information to a miniaturized CCD camera 24 located in the trailing end or handle 26 of surgical probe 10. Optical imaging guide 16, light guides 36 and photodetectors 22 are all contained within housing 28. Located in trailing end or handle 26 are directional indicators 30 and appropriate electronic circuitry 23 that, as described below, receives optical information from photodetectors 22, interprets that information and communicates proximity information to the surgeon during the surgical procedure. Cabling 32 provides the means for bringing power to surgical probe 10 as well as for extracting both directional and visual information to appropriate visual display 34 (represented schematically) from photodetectors 22 and CCD camera 24 respectively. Display 34 is located in the immediate vicinity of the surgeon so that he/she may receive visual information regarding the interior of the incision during the surgical procedure. Proximity information may be communicated directly in handle 26 using proximity display/alert system 30 (described below) located in handle 26 or via remote visual display 34.

Shown schematically in FIGS. 3, 4, and 5 are useful configurations for leading end 12 of intraoperative surgical probe 10. As shown in these Figures, leading end 12 comprises housing 28, optical imaging light guide 16 and an array of suitable radiation detector elements 14a–14d symmetrically located about optical imaging light guide 16 that together comprise radiation detector 14. While four radiation detectors 14a–14d are shown in each of the accompanying drawings, any suitable number of radiation detectors can be used. For ease of manufacture and simplicity of the electronic circuitry associated with radiation detector 14, it is preferred that from four to eight detectors be used, arrayed symmetrically about the four corners of the compass within housing 28. Specifically preferred from among this selection of possible radiation detector configurations is that depicted in FIG. 3 because it provides a maximum of radiation detector coverage (filing factor) resulting in the highest probe sensitivity with a minimum number of individual radiation detector elements 14a–14d and consequently a given small size.

Each of radiation detector elements 14a–14d are preferably comprised of scintillators made of but not limited to the following bright scintillators: YSO, YAP, GSO, LGSO, CsI(Tl), CsI(Na), NaI(Tl), $CaF_2(Eu)$, etc. Solid state materials such as CdZnTe, CdTe, $HgI_2$, and similar materials may also be used for this purpose. Scintillation visible light emitted by these materials when impacted by beta or gamma radiation is detected via transmission through fiber optic cables, fibers or rods 36 about optical imaging light guide 16 within housing 28 to photodetectors 22 in trailing end or handle 26. Directional information is obtained by electronic circuitry 23 polling the visible light produced by each of radiation detector elements 14 incorporated into handle 26 in leading end 12, comparing the readings thus obtained, and providing directional information dependent upon which of the radiation detecting elements 14 is yielding the highest level of visible light and consequently is most proximate the source of such radiation. In this fashion, individual elements 14a–14d provide information to the on-board circuitry to display directly on handle 26 of probe 10 and on a CCD monitor 34 (for comparison with structures seen in the visible image) the gradient of the radiation field, i.e. the direction of increasing radiation count and hence the location of the lesion.

FIGS. 4 and 5 depict alternative possible configurations for radiation detectors 14a–14d and optical image light guide 16 within leading end 12. Each of such configurations is useful and may be required depending upon the available configuration of radiation sensors 14a–14d. Whichever configuration is used, a minimum and therefore minimally intrusive size for the overall probe 12 is desirable. Thus, a probe 10 using an array of YSO scintillator crystals as depicted in FIG. 3 as radiation detector 14 and having a leading end outer diameter of about 10 mm and an inner optical imaging light guide aperture of about 4 mm provides a highly desirable size and configuration.

Radiation permeable window 18 must be permeable to beta particles and gamma radiation but physically strong enough and sufficiently light tight to protect underlying radiation sensor 14 from physical damage and photodetectors 22 from exposure to extraneous light. Typically, window 18 is about 10 to 50 microns thick and is fabricated from a plastic material such as Tedlar® or a light metal such as aluminum, beryllium, titanium, etc. To enhance collection of the scintillation light signal, window 18 should have good optical mirror or diffuser reflective properties.

It is practical to obtain this feature by separating the required mechanical properties of window 18 from the visible light optical properties by adding a second thin foil of a reflective material such as aluminized Mylar® or Teflon® (not shown). When used, the second thin foil is on the order of 10 microns thick.

The proximity display/alert system 30 may constitute any of a number of possible mechanisms including but not limited to LED, or LCD, either digital or linear, i.e. a number or a series of lights that light in increasing numbers as proximity increases, different colored lights which change as the probe approaches the area of beta/gamma emissions, e.g. from green, to yellow, to red as the probe approaches and comes into contact with cancerous tissue, analog as with a meter, or even audible with a repeating discreet signal whose frequency increases as the vicinity of a lesion is approached. Whatever of these possible systems is used, some directional information must be provided to guide the surgeon to the area of the lesion.

Housing 28 may be constructed of any suitable material of the type used for the housings of secondary electron multiplier devices. Metals, such as steel or aluminum are entirely suitable, so long as they are capable of maintaining containing the various operative elements within housing 28, while not otherwise interfering with the desired beta particle detection and measurement. In a particularly preferred embodiment, housing 28 is titanium.

As will be apparent to the skilled artisan, if optical imaging is not desired, a virtually equally useful directional probe can be constructed by simply omitting the centrally located optical imaging light guide 16 and utilizing a segmented radiation detector of the type described to obtain directional information as just described.

Figure 2:
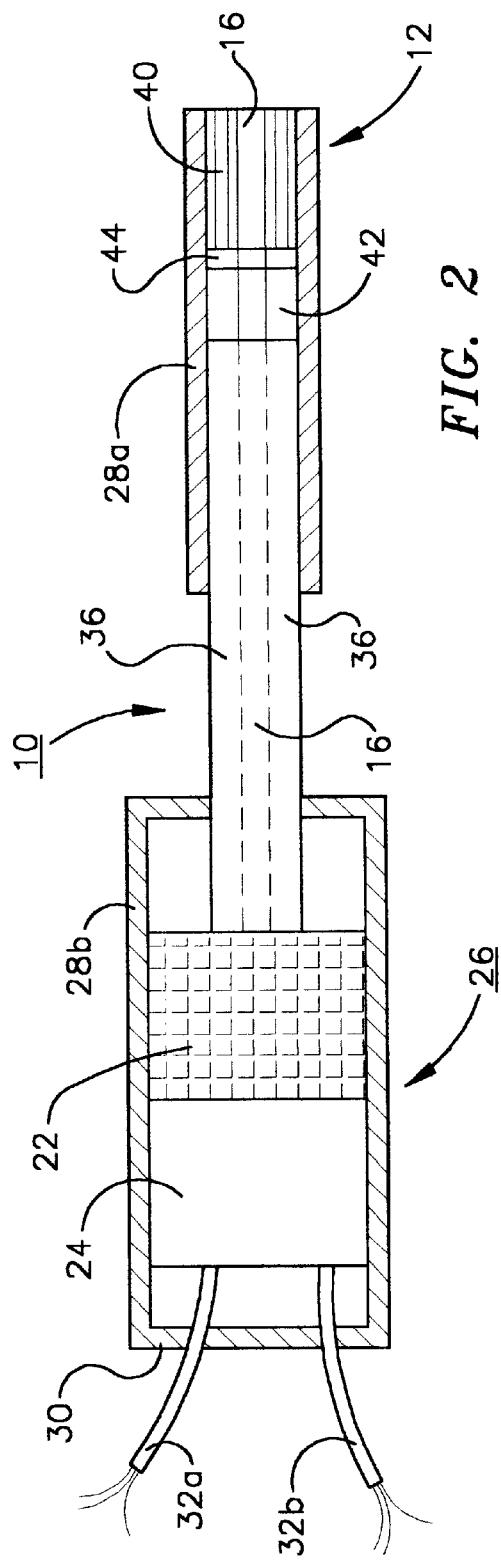
FIG. 2 is a schematic cross-sectional view of a second preferred embodiment of the intraoperative probe of the present invention.

An alternative embodiment of intraoperative surgical probe 10 is depicted in FIG. 2 wherein housing 28 has been divided into two portions: 1) 28a that encompasses a collimator 40, a phoswich type radiation sensor 42 capable of detecting both beta and gamma radiation protected by a radiation entrance window 44; and 2) 28b that encompasses photodetectors 22, CCD camera 24 and directional display/alert 30, the latter elements all connected by cables 32a and 32b to appropriate power and visual display devices (not shown). This configuration of probe 10 permits flexing of leading end 12 relative to handle 26 thereby providing additional less intrusive utility to probe 10.

As the invention has been described, it will be apparent to those skilled in the art that the same may be varied in many ways without departing from the spirit and scope of the invention. Any and all such modifications are intended to be included within the scope of the appended claims.

What is claimed is:

1. An intraoperative surgical probe comprising:
   a) a leading end comprising:
      I) a housing encompassing:
         A) a beta and gamma radiation permeable window;
         B) a visible light producing beta and gamma radiation detector comprising an array of radiation detector elements symmetrically arranged about a centrally located optical imaging light guide comprising a plurality of independent fiber optic conductors, each of said radiation detector elements independently connected to at least one separate photodetector via one of said independent fiber optic conductors; and
   b) a handle portion comprising:
      I) a housing encompassing:
         A) said separate photodetectors;
         B) a CCD camera;
         C) electronic circuitry;
         D) a proximity display or alert; and
   c) fiber optic conductors connecting said leading end and said handle such that visual information received by said optical imaging light guide in said leading end is transmitted to said CCD camera and visible light produced by said visible light producing radiation detector is transmitted to said photodetector producing an electronic output and said electronic output is interpreted by said electronic circuitry to provide directional information that is reported by said proximity display or alert.

2. The intraoperative surgical probe of claim 1 further including a visual display connected to said intraoperative surgical probe for displaying visual information generated by said CCD camera.

3. The intraoperative surgical probe of claim 2 further including a mechanism for displaying the output of said photodetector on said visual display.

4. The intraoperative probe of claim 1 wherein said radiation detector is a phoswich and further including a collimator in said leading end housing.

5. The intraoperative surgical probe of claim 1 wherein said leading end housing and said handle housing are separate components connected by said fiber optic conductors.

6. The intraoperative surgical probe of 1 wherein said proximity display comprises an LED or LCD or an audible signal.

7. The intraoperative surgical probe of claim 1, wherein said radiation detector comprises a symmetrical array of four independent radiation detector elements arrayed tightly about said centrally located optical imaging light guide.

8. The intraoperative surgical probe of claim 1 wherein said radiation detector elements comprise a scintillator selected from the group consisting of YSO, YAP, GSO, LGSO, CsI(Tl), CsI(Na), NaI(Tl), $CaF_2(Eu)$, CdZnTe, CdTe, and $HgI_2$.

* * * * *